(12) United States Patent
Kweon et al.

(10) Patent No.: US 11,642,180 B2
(45) Date of Patent: May 9, 2023

(54) DEVICE AND METHOD FOR DETECTING GUIDEWIRE

(71) Applicants: THE ASAN FOUNDATION, Seoul (KR); University of Ulsan Foundation For Industry Cooperation, Ulsan (KR); Medipixel, Inc., Seoul (KR)

(72) Inventors: Jihoon Kweon, Seoul (KR); Young Eon Kim, Seoul (KR); Kyo Seok Song, Seoul (KR)

(73) Assignees: THE ASAN FOUNDATION, Seoul (KR); University of Ulsan Foundation For Industry Cooperation, Ulsan (KR); Medipixel, Inc., Seoul (KR)

( * ) Notice: Subject to any disclaimer, the term of this patent is extended or adjusted under 35 U.S.C. 154(b) by 0 days.

(21) Appl. No.: 17/752,344

(22) Filed: May 24, 2022

(65) Prior Publication Data
US 2022/0378514 A1    Dec. 1, 2022

(30) Foreign Application Priority Data
May 25, 2021    (KR) .......................... 10-2021-0067079

(51) Int. Cl.
*A61B 34/20* (2016.01)
*G06T 7/73* (2017.01)
*A61B 6/00* (2006.01)

(52) U.S. Cl.
CPC ............... *A61B 34/20* (2016.02); *A61B 6/463* (2013.01); *A61B 6/481* (2013.01); *A61B 6/504* (2013.01);
(Continued)

(58) Field of Classification Search
CPC ......... A61B 34/20; A61B 6/463; A61B 6/504; A61B 2034/2065; G06T 7/74; G06T 2207/30101
See application file for complete search history.

(56) References Cited

U.S. PATENT DOCUMENTS

2013/0223702 A1    8/2013   Holsing et al.
2013/0303893 A1   11/2013   Duindam et al.
(Continued)

FOREIGN PATENT DOCUMENTS

JP    2014508020 A    4/2014
JP    2016087139 A    5/2016
(Continued)

OTHER PUBLICATIONS

"An Automatic Algorithm for Vessel Segmentation in X-Ray Angiogram using Randon Forest", Jung, et al. Journal of Biomedical Engineering Research, http://dx.doi.org/10.9718/JBER, 2015.36.4. 79. pp. 79-85.

(Continued)

*Primary Examiner* — Amelie R Davis
(74) *Attorney, Agent, or Firm* — George McGuire

(57) ABSTRACT

An electronic device includes a processor configured to generate a position movement prediction field indicating prediction of a potential positional change of a branch path by a patient's biological activity for one or more branch paths based on a blood vessel image of a reference frame, correct guidewire information extracted from a blood vessel image of a target frame with respect to a catheter position of the reference frame, and select a branch path to dispose the guidewire information, among one or more branch paths of a blood vessel region based on the position movement prediction field and the corrected guidewire information; and a display configured to visualize the guidewire information on the selected branch path.

19 Claims, 17 Drawing Sheets

(52) U.S. Cl.
CPC ........ *G06T 7/74* (2017.01); *A61B 2034/2065* (2016.02); *G06T 2207/30101* (2013.01)

(56) References Cited

U.S. PATENT DOCUMENTS

2015/0178886 A1* 6/2015 Pfister ....................... G06T 5/50
382/132
2020/0410666 A1* 12/2020 Wagner ................... A61B 6/12

FOREIGN PATENT DOCUMENTS

| | | | |
|---|---|---|---|
| JP | 2021052825 | A | 4/2021 |
| KR | 101892631 | B | 8/2018 |
| KR | 102161401 | B | 9/2020 |
| KR | 102305965 | B1 | 9/2021 |
| WO | 2005070318 | A1 | 8/2005 |
| WO | 2005082246 | A1 | 9/2005 |
| WO | 2017030913 | A2 | 2/2017 |

OTHER PUBLICATIONS

Extended European Search Report of EP 22 17 4873. dated Jan. 27, 2023. pp. 1-9.

* cited by examiner

DEVICE AND METHOD FOR DETECTING GUIDEWIRE

CROSS-REFERENCE TO RELATED APPLICATION

This application claims the benefit of Korean Patent Application No. 10-2021-0067079 filed on May 25, 2021, in the Korean Intellectual Property Office, the entire disclosure of which is incorporated herein by reference for all purposes.

BACKGROUND

1. Field of the Invention

One or more example embodiments relate to a guidewire detecting technique is provided.

2. Description of the Related Art

During a treatment which is performed by inserting a surgical operation tool in a body and checking a position of the surgical operation tool through an X-ray, a structure and a position of a blood vessel are identified by injecting a contrast. However, the blood vessel is identified only for a short time after injecting the contrast. Further, the position of the blood vessel in a heart area and/or an area adjacent to the heart may be irregularly changed due to the influence of heartbeat and breathing. Accordingly, in order to periodically identify a shape of the blood vessel, the contrast may be repeatedly injected. In a cardiovascular interventional procedure, it is very important to move a guidewire to a lesion area. Even though the contrast is repeatedly injected, it is difficult to clearly identify the blood vessel until a next contrast is injected so that it may be difficult to manipulate the guidewire to reach a desired location. This is because it is difficult to identify a position of a tip of the guidewire located with respect to the blood vessel.

The above-described background is held or acquired by the inventor during the process of deriving the present disclosure and is not necessarily a known technology which has been disclosed to the general public prior to this application.

SUMMARY

According to an aspect, there is provided an electronic device including a processor configured to generate a position movement prediction field indicating prediction of a potential positional change of a branch path by a patient's biological activity for one or more branch paths based on a blood vessel image of a reference frame, correct guidewire information extracted from a blood vessel image of a target frame with respect to a catheter position of the reference frame, and select a branch path to dispose the guidewire information, among one or more branch paths of a blood vessel region based on the position movement prediction field and the corrected guidewire information; and a display configured to visualize the guidewire information on the selected branch path.

The electronic device may further include an image acquiring unit configured to acquire coronary angiographic images of the reference frame and the target frame as blood vessel images of the reference frame and the target frame.

The processor may generate an entire path length map indicating a path length to points in a segmented blood vessel region from the blood vessel image of the reference frame and generate the position movement prediction field for each of one or more branch paths of the blood vessel region based on the entire path length map.

The processor may extract a blood vessel region image in which the blood vessel region is segmented from the blood vessel image of the reference frame, detect a catheter position from the blood vessel image of the reference frame based on a first machine learning model to set the catheter position as a reference position, and generate an entire path length map indicating a path length from a start position set using the reference position to points in the blood vessel region.

The processor may acquire a branch path length map for each of one or more branch paths from the generated entire path length map and generate a position movement prediction field of the corresponding branch path based on the branch path length map for each of one or more branch paths.

The processor may determine the same value as the path length value of the corresponding point in the position movement prediction field for each branch path, as a predictive value of a position predicted that each point in the branch path is potentially moved by a biological activity.

The processor may determine each predictive value of the position movement prediction field based on Euclidean distance transform between each point in the branch path and a point outside the branch path.

The processor may detect a catheter position of the reference frame from the blood vessel image of the reference frame based on a first machine learning model, detect a catheter position of the target frame from the blood vessel image of the target frame based on the first machine learning model, and correct the guidewire information based on a difference between the catheter position of the reference frame and the catheter position of the target frame.

The processor may extract the guidewire information from the blood vessel image of the target frame based on a second machine learning model which is different from the first machine learning model.

The processor may extract a guidewire candidate region for one or more branch paths based on the corrected guidewire information and the generated position movement prediction field and select one branch path among one or more branch paths, based on comparison between the guidewire candidate region for one or more branch paths and the guidewire information.

The processor may acquire a plurality of predictive values corresponding to a guidewire in the corresponding branch path by mapping the corrected guidewire information on the position movement prediction field for each of one or more branch paths and extract the guidewire candidate region of the branch path based on the plurality of acquired predictive values.

The processor may extract a guidewire candidate region of the corresponding branch path based on a minimum value and a maximum value among the plurality of acquired predictive values.

The processor may calculate a distance score between the guidewire candidate region for one or more branch paths and the guidewire information and select a branch path having a candidate region indicating the highest distance score among the guidewire candidate regions.

The processor may select a branch path based on a comparison history between the guidewire candidate region of each branch path in a previous frame of the target frame and the guidewire information and a comparison result between the guidewire candidate region of each branch path in the target frame and the guidewire information.

The processor may apply a first weight to a first comparison score in a first previous frame which precedes the target frame by one frame difference and apply a second weight which is different from the first weight to a second comparison score in a second previous frame which precedes the target frame by a second frame difference which is larger than the first frame difference, and select the branch path using a fused result value based on a first partial score obtained by applying the first weight to the first comparison score and a second partial score obtained by applying the second weight to the second comparison score.

The processor may fit the guidewire information to a center line of the selected branch path and the display may overlay the fitted guidewire information on the branch path.

The target frame is a frame after the reference frame.

The reference frame may indicate a frame corresponding to a timing when a contrast is injected into the patient.

According to another aspect, there is provided a guidewire detecting method performed by an electronic device including: generating a position movement prediction field indicating prediction of a potential positional change of a branch path by a patient's biological activity for one or more branch paths based on a blood vessel image of a reference frame; correcting guidewire information extracted from a blood vessel image of a target frame with respect to a catheter position of the reference frame; selecting a branch path to dispose the guidewire information, among one or more branch paths of a blood vessel region based on the position movement prediction field and the corrected guidewire information; and visualizing the guidewire information on the selected branch path.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
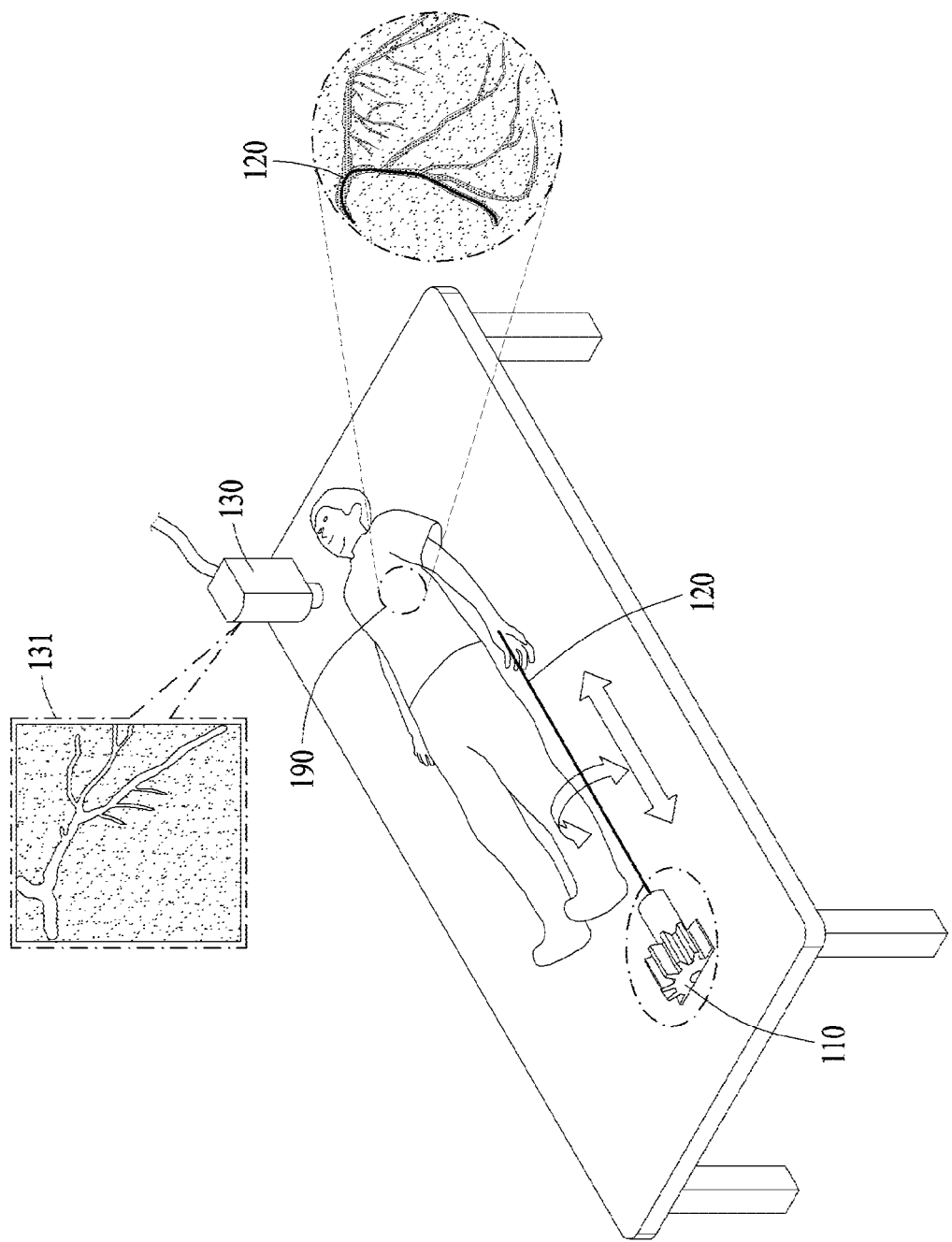
FIG. 1 illustrates a medical tool control system according to an example embodiment.

Specific structural or functional descriptions for example embodiments are provided for the purpose of illustration only and may be changed in various forms to be implemented. Accordingly, an actually implemented form is not limited only to the specific disclosed example embodiment and the scope of the present specification includes changes, equivalents, or substitutes included in a technical spirit described in the example embodiments.

Even though the terms of first or second are used to describe various components, the terms should be interpreted only to distinguish one component from the other component. For example, a first component may be referred to as a second component, and similarly, a second component may be referred to as a first component.

It should be understood that, when it is described that an element is "connected" to another element, the element may be directly coupled or directly connected to the other element or coupled or connected to the other element through a third element.

A singular form may include a plural form if there is no clearly opposite meaning in the context. In the present specification, it should be understood that terms "include" or "have" indicates that a feature, a number, a step, an operation, a component, a part or the combination those of described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terminologies which are defined in a generally used dictionary should be interpreted to have the same meaning as the meaning in the context of the related art but are not interpreted as an ideally or excessively formal meaning if it is not clearly defined in this specification.

Hereinafter, example embodiments will be described in detail with reference to the accompanying drawings. In description with reference to accompanying drawings, the same components are denoted by the same reference numerals regardless of the reference numeral and a duplicated description thereof will be omitted.

FIG. 1 illustrates a medical tool control system according to an example embodiment.

A medical tool control system 100 according to an example embodiment is a system 100 for controlling a movement of a medical tool 120 and may include a blood vessel imaging device 130 and a medical tool control device. Even though in FIG. 1, for the convenience of description, only a driver 110 of the medical tool control device is illustrated, it is not limited thereto.

The blood vessel imaging device 130 is a device which captures a blood vessel image 131. The blood vessel image 131 indicates an image obtained by capturing a blood vessel of a target object (for example, a subject 190). The blood vessel imaging device 130 may capture the blood vessel image 131 using coronary angiography (hereinafter, abbreviated as "CAG") or magnetic resonance imaging (hereinafter, abbreviated as "MRI"). In the blood vessel image 131, not only the blood vessel but also the medical tool 120 may be captured.

In the present specification, the medical tool 120 is a member which is inserted into the blood vessel, for example, may be a surgical tool which is moved and/or operated by the manipulation and/or a given instruction of an operator (for example, a doctor). For example, the medical tool 120 is a medical wire and may include a catheter and a guidewire. The catheter may refer to a medical device which provides a passage to assist the insertion and accessing of a balloon catheter and/or a guidewire in a destination affected area in the blood vessel. In the present specification, the catheter mainly refers to an interventional catheter having a lumen to transfer the guidewire into the blood vessel for a percutaneous treatment (for example, percutaneous vascular interventional therapy or percutaneous transluminal angioplasty). The guidewire refers to a guidance wire which guides a transfer path to allow a medical tool such as a catheter, a balloon, or a stent to reach a destination affected area through a vasculature including a blood vessel. For reference, the catheters may be transferred together with guidewires in major blood vessels, such as the aorta and/or coronary arteries, to reach peripheral blood vessels. The guidewire may be transferred through a lumen of the catheter and a tip of the guidewire may be inserted and moved to the peripheral blood vessel. However, the catheter and the guidewire are not limited to those described above.

The medical tool control device may move the medical tool 120 inserted into the blood vessel to a destination part in the blood vessel. Even though in FIG. 1, it is illustrated that the medical tool 120 is inserted into a blood vessel of a wrist of the subject 190, it is not limited thereto so that the medical tool may be inserted through a blood vessel of a lower body of the subject 190. A destination part may be a part in which a disease or a lesion is potentially or explicitly present.

The medical tool control device may move the tip of the medical tool 120 to the destination part. The medical tool control device may include a robot which transfers the medical tool 120. For example, the medical tool control device may transfer the medical tool 120 through the driver 110. The driver 110 may include one or more motors and a mechanical power transfer structure which converts a torque of the motor into a straight-line motion and/or a rotational motion of a desired axis. For example, the driver 110 may be driven to push the medical wire 120 in response to a forward command to allow the medical tool 120 to go forward. The driver 110 may be driven to pull the medical wire 120 in response to a backward command to allow the medical tool 120 to go backward. The driver 110 may be driven to rotate the medical wire 120 with a longitudinal axis of the medical wire 120 as a reference axis in response to the rotate command to rotate the medical tool 120. However, it is not limited thereto and the medical tool 120 may be transferred by the manipulation of the medical personnel.

The medical tool control system 100 according to the example embodiment may provide an accurate position of the guidewire to a user (for example, a medical personnel) in an interventional therapy and the like that uses a catheter to treat a disease such as a cardiovascular disease, a cerebrovascular disease, and a bile duct disease in a state in which an operator is spaced away from an imaging device using radiation.

The medical tool control system 100 according to the example embodiment includes an electronic device (not illustrated) and the electronic device (not illustrated) is integrally implemented with the blood vessel imaging device 130 to capture a blood vessel image or receive a blood vessel image from the blood vessel imaging device 130. The electronic device (not illustrated) may estimate an accurate position of the tip of the guidewire according to heartbeat during the cardiovascular interventional therapy. For example, when the contrast is initially injected into the patient, the electronic device (not illustrated) automatically may analyze a structure of a blood vessel and then estimate the position of the guidewire in real-time. The electronic device (not illustrated) overlays a real-time guidewire position on the initially acquired blood vessel structure to provide an accurate position of the guidewire in the blood vessel to the user (for example, an operator) even during a time period when the contrast is not injected. Accordingly, the electronic device (not illustrated) according to the example embodiment may accurately display the position of the tip of the guidewire in real-time to reduce an amount of injected contrast and lower a skill level required for the operator. The electronic device (not illustrated) may also be referred to as a guidewire detecting device.

Figure 2:
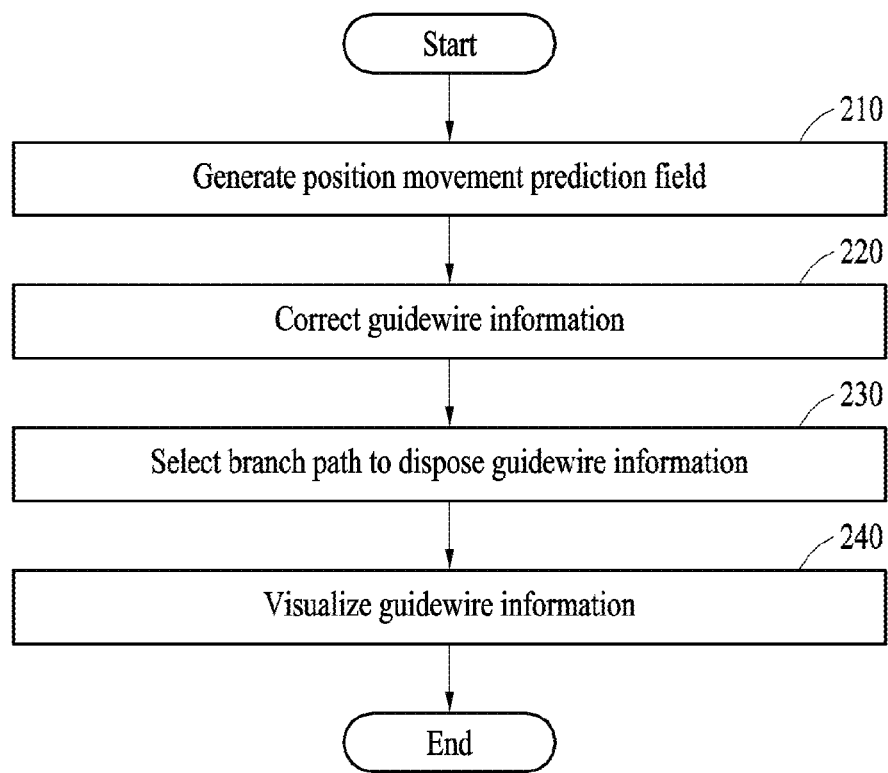
FIG. 2 is a flowchart for explaining a guidewire detecting method according to an example embodiment.
Figure 3:
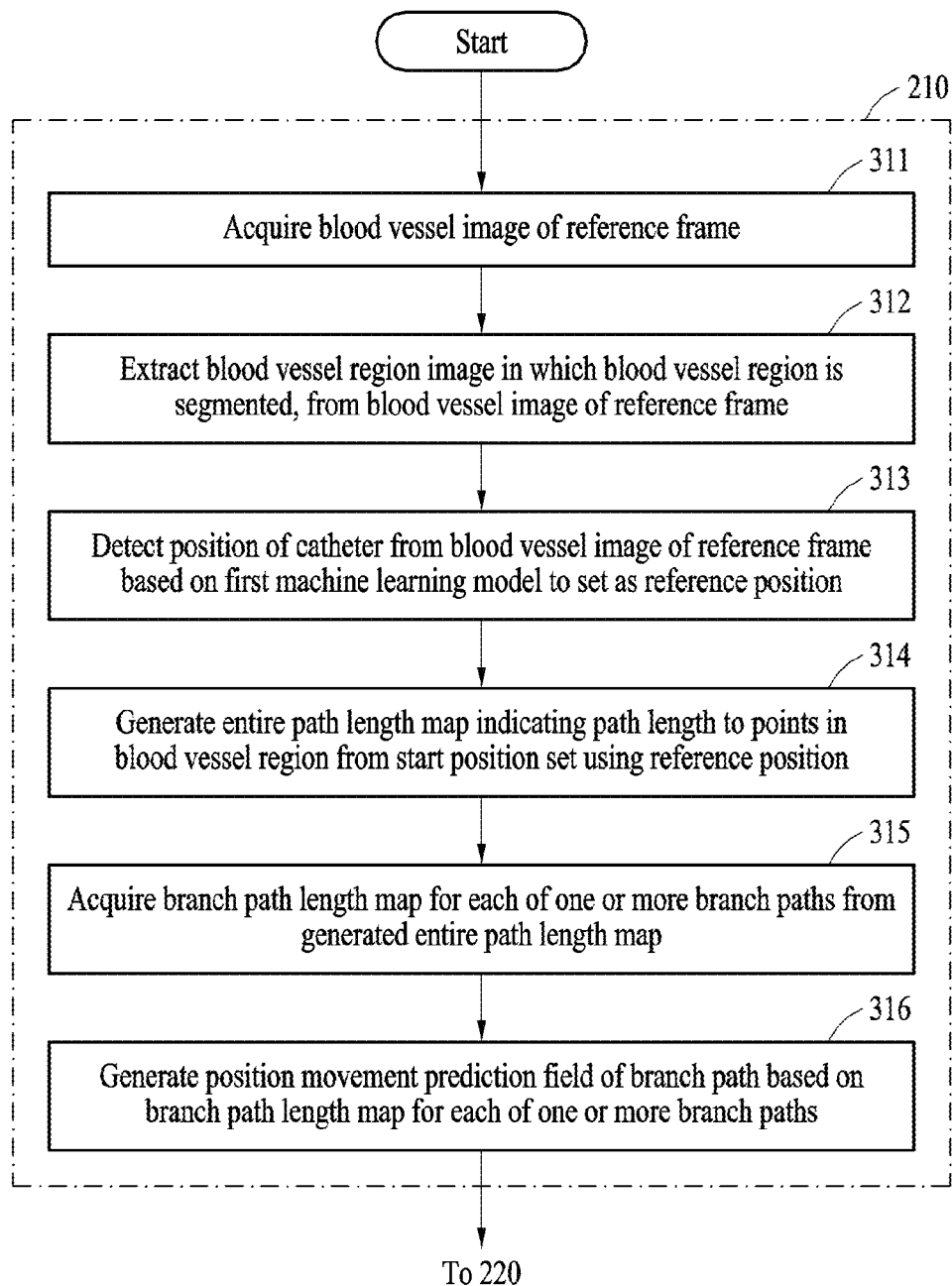
FIGS. 3 to 9 explain generation of a position movement prediction field according to an example embodiment.

FIG. 2 is a flowchart for explaining a guidewire detecting method according to an example embodiment.

First, in step 210, the electronic device may generate a position movement prediction field. The electronic device according to the example embodiment may generate the position movement prediction field which indicates a prediction of a potential positional change of a branch path due to a patient's biological activity for one or more branch paths (e.g., every branch path) based on a blood vessel image of a reference frame. For example, the electronic device may generate an entire path length map indicating a path length to points in a segmented blood vessel region from the blood vessel image of the reference frame. The electronic device may generate the position movement prediction field for each of one or more branch paths of the blood vessel region based on the entire path length map. The position movement prediction field will be described in detail with reference to FIG. 9.

In step 220, the electronic device may correct guidewire information. For example, the electronic device may correct the guidewire information extracted from the blood vessel image of a target frame based on a catheter position of the reference frame.

Next, in step 230, the electronic device may select a branch path to dispose the guidewire information. For example, the electronic device may select the branch path to dispose the guidewire information, among one or more branch paths of the blood vessel region, based on the position movement prediction field and the corrected guidewire information.

In step 240, the electronic device may visualize the guidewire information. For example, a display of the electronic device may visualize the guidewire information on the selected branch path.

Hereinafter, the above-described operations will be described in detail.

FIGS. 3 to 9 explain generation of a position movement prediction field according to an example embodiment.

In step 311, the electronic device may acquire a blood vessel image 410 of the reference frame. For example, the electronic device may capture the blood vessel image 410 for a target patient from the reference frame or receive the blood vessel image from a blood vessel imaging device. The reference frame may indicate a frame corresponding to a timing when a contrast is injected into the patient. As described above, a blood vessel of the patient may be exposed from a blood vessel image captured for a predetermined time of period after injecting the contrast into the patient as described above.

Figure 4:
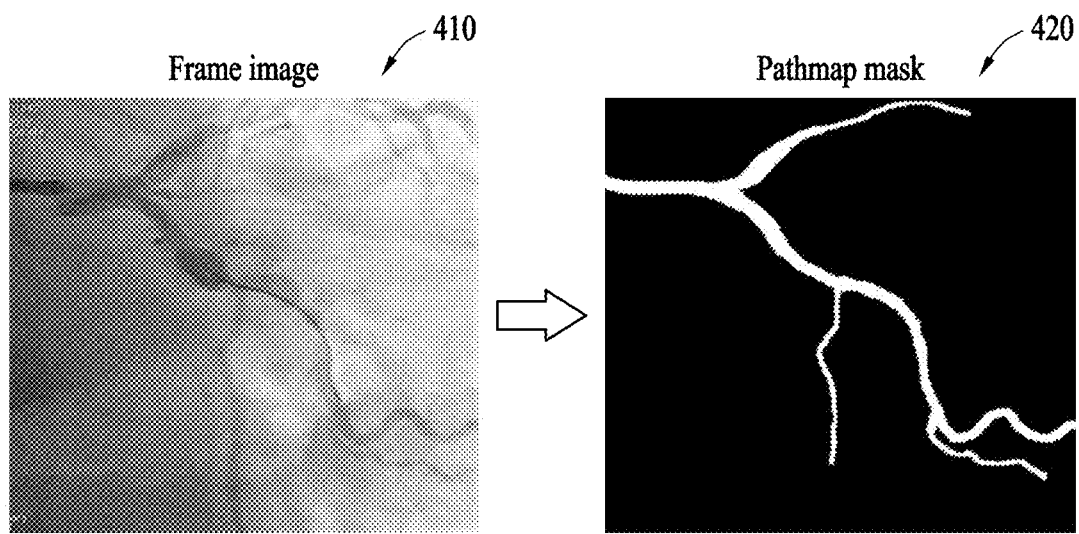

In step 312, the electronic device may extract a blood vessel region image 420 in which a blood vessel region is segmented from the blood vessel image 410 of the reference frame. For example, as illustrated in FIG. 4, the electronic device may acquire a blood vessel region image 420 from a blood vessel image 410 (for example, a coronary angiography (CAG) image) acquired from the reference frame. The blood vessel region image 420 is an image representing an area belonging to the blood vessel and in FIG. 4, is illustrated as a masking image in which the blood vessel region is represented with white and the remaining area is represented with black, but is not limited thereto.

Figure 5:
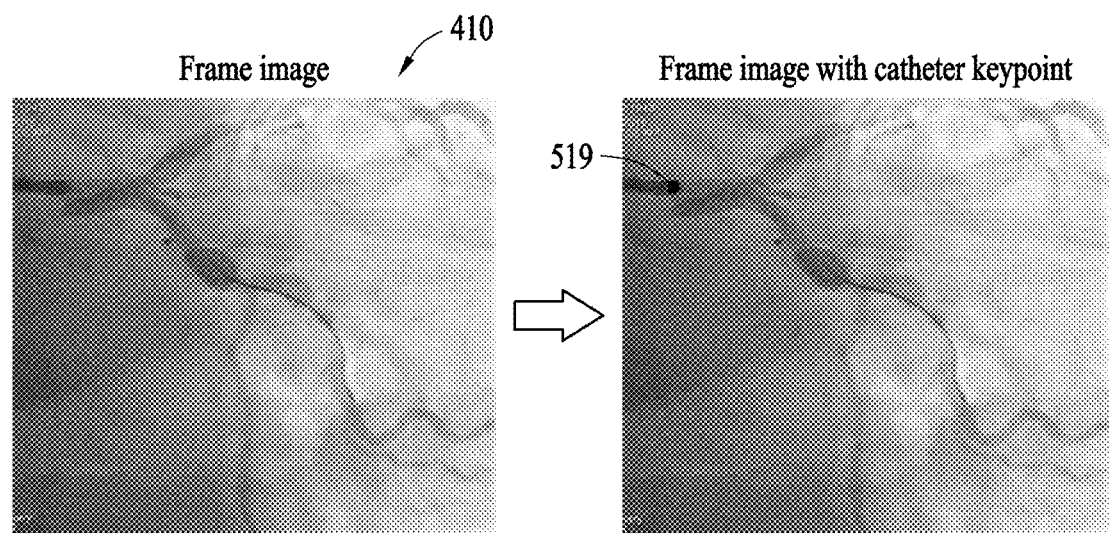

Next, in step 313, the electronic device may detect the catheter position 519 from the blood vessel image 410 of the reference frame based on a first machine learning model as illustrated in FIG. 5 to set as a reference position. For example, the electronic device may detect a coordinate in which the tip of the catheter is located from the coronary angiographic image as a reference position. The first machine learning model is a machine learning model which is designed and trained to detect the catheter position, and for example, may include a neural network. The first machine learning model may output a coordinate value indicating the catheter position in each blood vessel image in response to the input of the blood vessel image 410 of the reference frame and/or a blood vessel image of a target frame.

The neural network may be an example of a deep neural network (DNN). DNN may include a fully connected network, a deep convolutional network, a recurrent neural network, and the like. The neural network may map input data and output data having a non-linear relationship based on the deep learning to perform various tasks (for example, detection of a catheter position and/or extraction of a guidewire region, etc.). The deep learning may map the input data and the output data by means of supervised or unsupervised learning as the machine learning technique.

The neural network includes an input layer, a hidden layer, and an output layer. Each of the input layer, the hidden layer, and the output layer has a plurality of nodes. The hidden layer may include a large number of layers. The nodes of layers excluding the output layer in the neural network may be connected to nodes of the next layers through links for transmitting an output signal and the links may connect the layers with various structures. An output of an activation function regarding weighted inputs of the nodes included in a previous layer may be input to nodes included in the hidden layer. A weight may be referred to as a parameter of the neural network. The activation function may include sigmoid, hyperbolic tangent (tan h), and rectified linear unit (ReLU), and the activation function may give the non-linearity to the neural network.

When the neural network has sufficient width and weight, the neural network may have a capacity enough to implement an arbitrary function. When the neural network learns sufficient training data by means of an appropriate training process, an optimal inference performance may be achieved. In the present specification, the neural network is mainly described as a machine learning model, but it is not limited thereto. For reference, a second machine learning model to be described below may be designed to be different from the first machine learning model.

Figure 6:
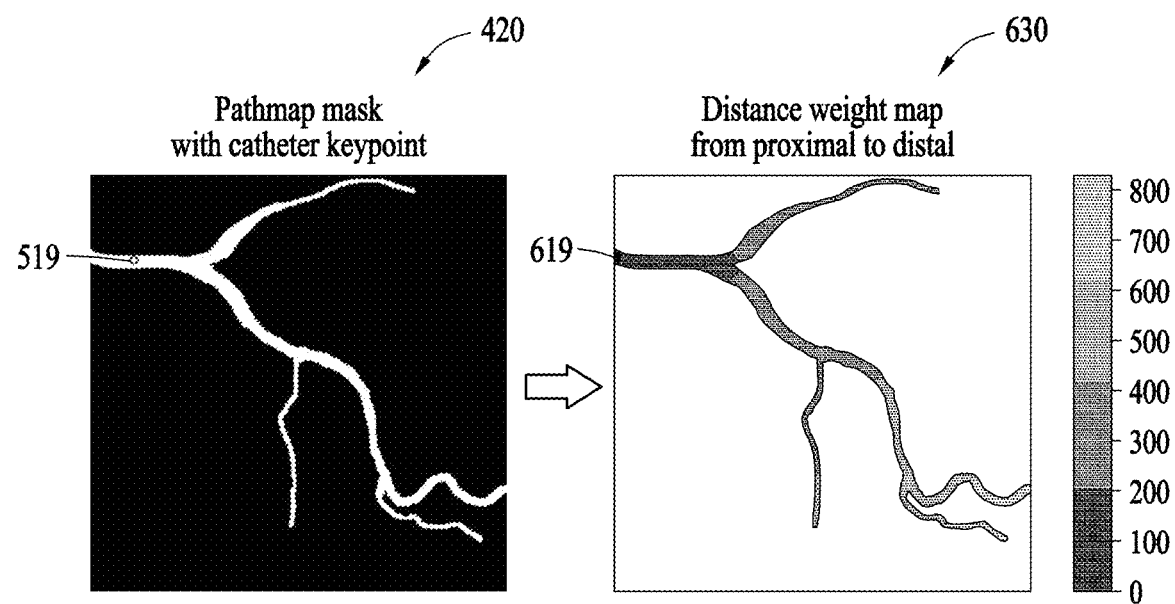

Next, in step 314, the electronic device may generate an entire path length map 630 indicating a path length to points in the blood vessel region from a start position 619 set using the reference position, as illustrated in FIG. 6. The electronic device may set a position in the blood vessel region of the blood vessel region image which is most adjacent to the ex-vivo based on the reference position, as the start position 619. In other words, the electronic device may determine a position where the blood vessel starts in the blood vessel region located in the opposite side to the end of the blood vessel with respect to the reference location as the start position 619. Generally, the catheter and the guidewire may be percutaneously inserted into a portion closer to the heart than the terminal of the body so that the start position 619 may be a position most adjacent to the ex-vivo and/or the operator in the blood vessel region of the blood vessel region image. However, the start position 619 is not limited thereto.

The electronic device may calculate a path length from the start position 619 which has been described above for each pixel of the above-described blood vessel region image to the position corresponding to each pixel. A path length from the start position 619 to one pixel is a length of a path (for example, a shortest path) from the reference position to a pixel position of the corresponding pixel in a segmented/extracted blood vessel region and may be a path through which the guidewire moves from the reference position to the position corresponding to the pixel. For example, the path length may be the number of pixels included in the shortest path from the reference position to each pixel position. However, the path length is not limited thereto. The path length to a point and/or the pixel position adjacent to the start position 619 may be short and a path length to a point and/or a pixel position adjacent to the end position of the branch may be long. In other words, the farther the point from the start position 619, the larger the value of the path length.

The electronic device may generate the entire path length map 630 indicating a path length for every point in the blood vessel region. The entire path length map 630 may be a map including a path length for points belonging to branch paths for every branch. As it will be described below, the electronic device may generate an entire path length map 630 for the entire path and a branch path length map for a path of a part of the branches. Individual pixel values of the path length map (for example, the entire path length map 630 and a branch path length map) may have a value indicating a length according to a path from the start position 619 to a position corresponding to the pixel.

In step 315, the electronic device may acquire the branch path length map for each of one or more branch paths from the generated entire path length map 630. According to the example embodiment, the electronic device may identify the branch path for every branch and segment the branch path length map corresponding to the identified branch path from the entire path length map 630.

Figure 7:
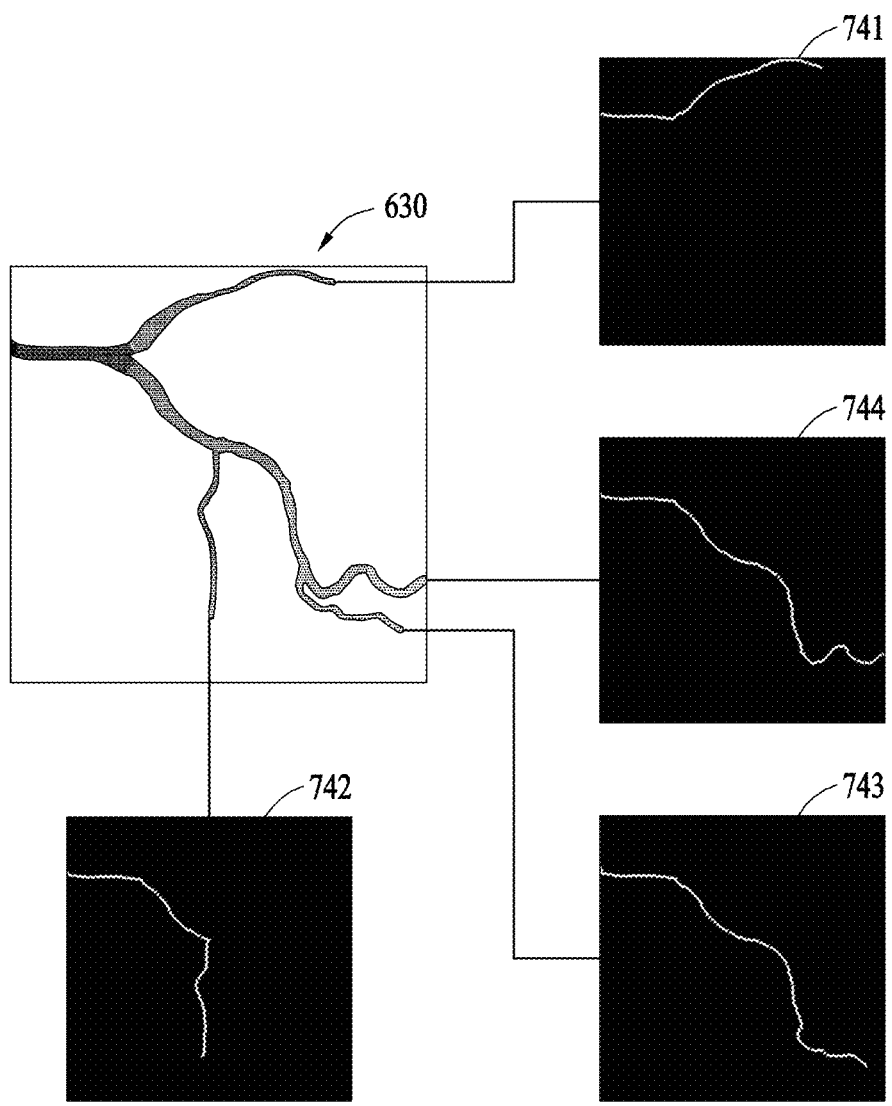

For example, the electronic device may extract a branch path corresponding to each of a plurality of branches extracted from the blood vessel image and/or the entire path length map 630. The branch path may be a path connected from the start position to an end position of each branch extracted from the blood vessel region image. The electronic device may extract the above-described branch path along a center line of the blood vessel as illustrated in FIG. 7. For example, in FIG. 7, a first branch path 741, a second branch path 742, a third branch path 743, and a fourth branch path 744 may be extracted for four branches.

Figure 8:
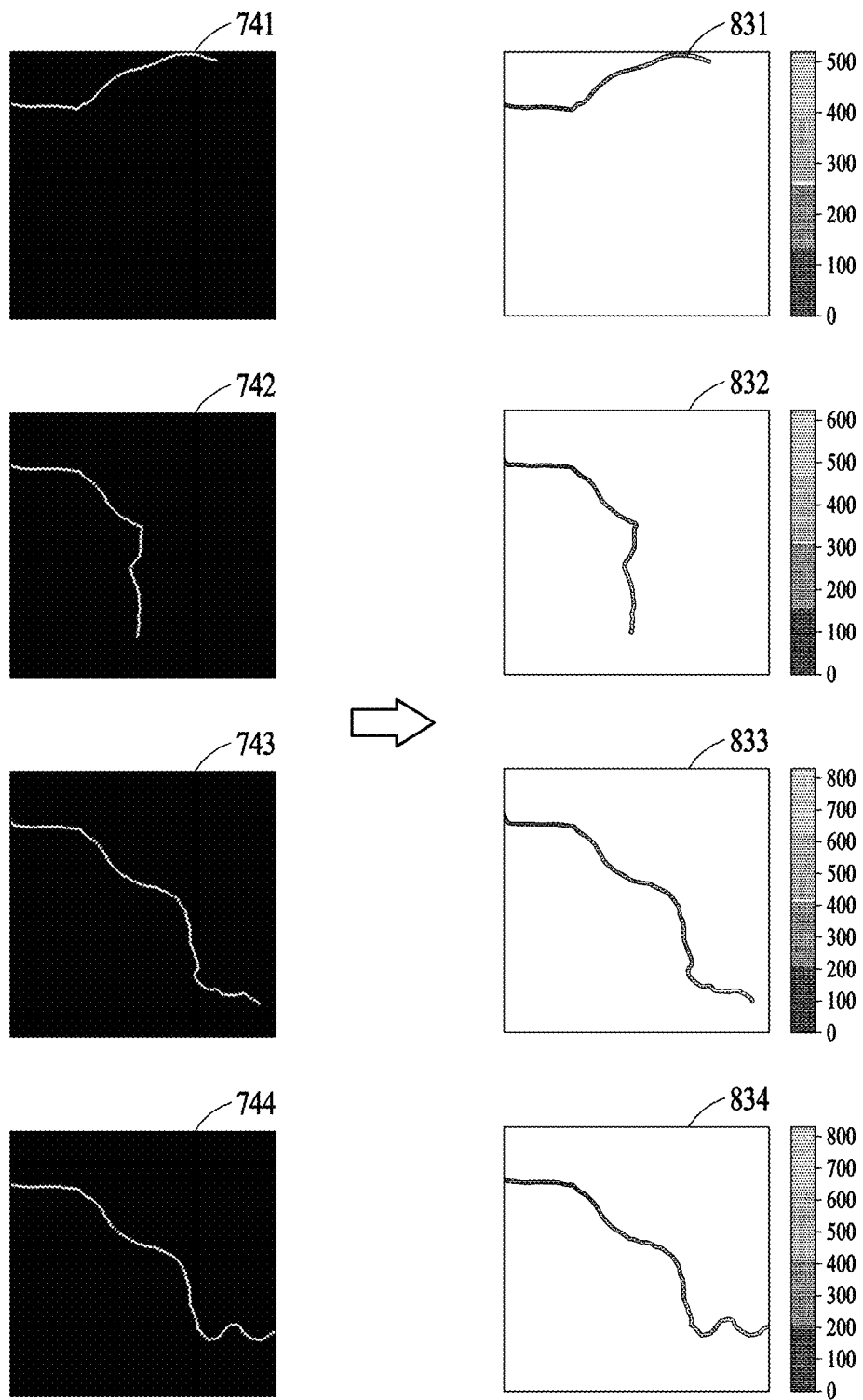

The electronic device may acquire a path length map for each branch path from the entire path length map 630 using the extracted branch path. The path length map for a single branch path may be also referred to as a branch path length map. For example, the electronic device may acquire a branch path length map corresponding to the branch path by extracting a partial map corresponding to each branch path from the entire path length map 630. The electronic device may generate a branch path mask image in which a pixel value of a portion corresponding to the branch path is 1 and a pixel value of the remaining portion is 0 and generate the branch path length map of the corresponding branch path by element-wise product between the branch path mask and the entire path length map 630. For example, as illustrated in FIG. 8, the electronic device may acquire a first branch path length map 831 for the first branch path 741, a second branch path length map 832 for the second branch path 742, a third branch path length map 833 for the third branch path 743, and a fourth branch path length map 834 for the fourth branch path 744.

Figure 9:
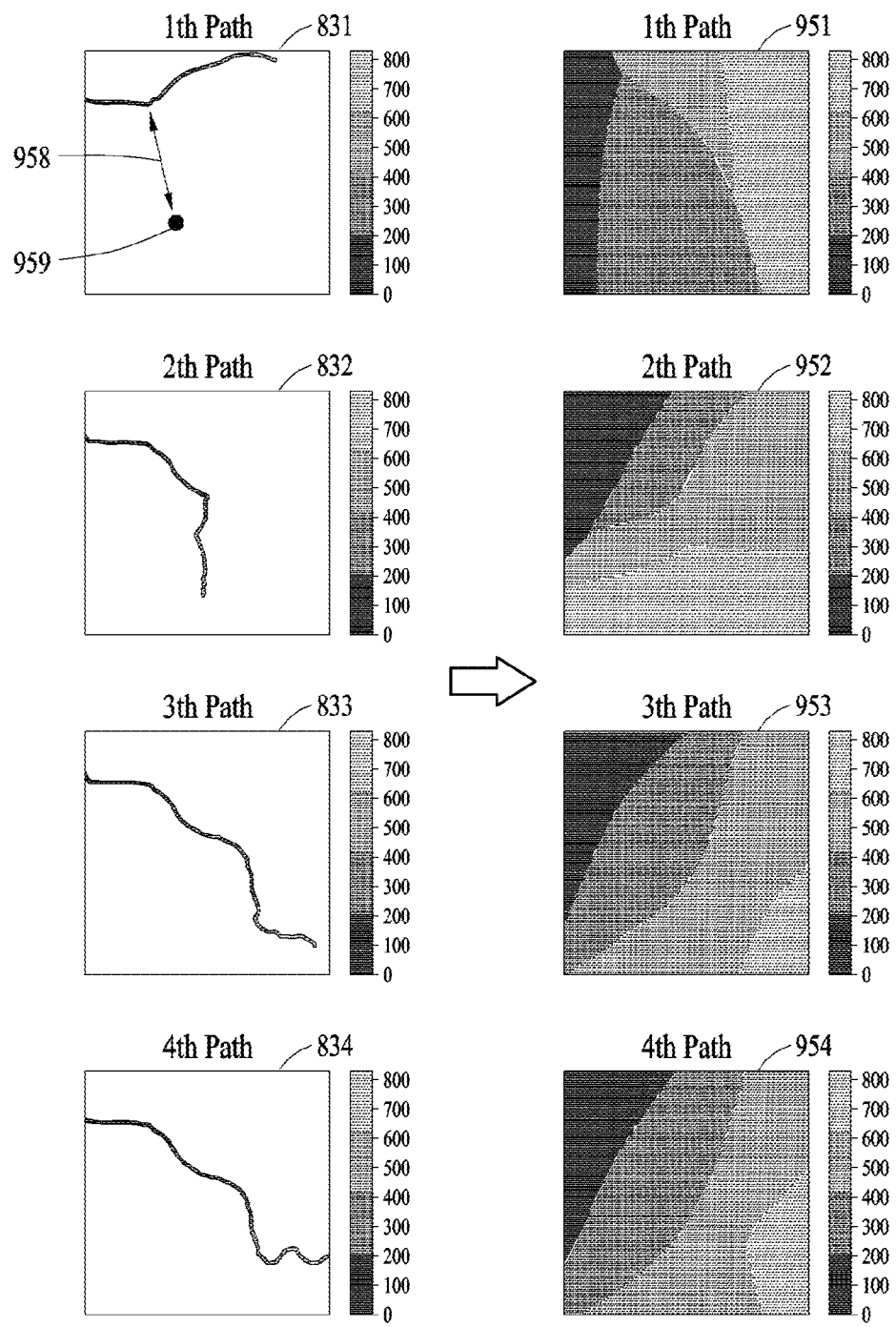

In step 316, the electronic device may generate a position movement prediction field of the corresponding branch path based on the branch path length map for each of one or more branch paths as illustrated in FIG. 9. The position movement prediction field for an arbitrary branch path is a field representing a prediction of a potential positional change of the corresponding branch path due to a patient's biological activity and may indicate a position and/or an area to which a point belonging to the corresponding branch path of the blood vessel image of the reference frame, a blood vessel branch, and the blood vessel potentially move due to the biological activity of a patient whose blood vessel is captured. For example, the position movement prediction field is a field having the same resolution as the path length map (for example, the entire path length map and the branch path length map) and may be a set of the same number of predictive values as the pixels included in the path length map. A predictive value for an arbitrary point of the branch path may have a value indicating a pixel which may potentially move to the corresponding point by the biological activity, among pixels belonging to the branch path in the branch path length map. For example, the electronic device may determine the predictive value of a position and/or a region which is predicted that each point in the corresponding branch path potentially moves due to the biological activity, in the position movement prediction field for each branch path, to be the same value as the path length value of the corresponding point. In other words, in the present specification, the position movement prediction field may be interpreted as a field where a position perpendicular to the longitudinal axis of the branch path is predicted as an area where the branch path potentially and temporally exists due to the heartbeat.

According to the example embodiment, the electronic device may determine each predictive value of the position movement prediction field based on Euclidean distance transform between each point in the branch path and a point outside the branch path. For example, the electronic device may determine a predictive value of a target point 959 based on a Euclidean distance 958 between the target point 959 and points in the branch in the branch path length map. For example, the predictive value in the target point 959 in the position movement prediction field for one branch path may have a path length value of a pixel in a pixel position closest (for example, having the shortest Euclidean distance 958) to the pixel position corresponding to the target point 959, among pixels belonging to the corresponding branch path in the corresponding branch path length map. In FIG. 9, the electronic device may generate a first position movement prediction field 951 from the first branch path length map 831, a second position movement prediction field 952 from the second branch path length map 832, a third position movement prediction field 953 from the third branch path length map 833, and a fourth position movement prediction field from the fourth branch path length map 834. In the present specification, in the path length map and the position movement prediction field, the closer to the start point, the darker the color is illustrated and the farther from the start point, the brighter the color is illustrated. In other words, a small value (for example, a value close to 0) is represented by a dark color and a large value (for example, a value close to 1000) is represented by a bright color.

The above-described position movement prediction field may implicate an equivalent area in the outside and the inside of the blood vessel along the path length. In other words, the position movement prediction field may be used as a clue to estimate an actual position of the guidewire in the target frame which looks like it is located outside the blood vessel region identified in the reference frame due to the biological activity (for example, heartbeat and/or breath).

Figure 10:
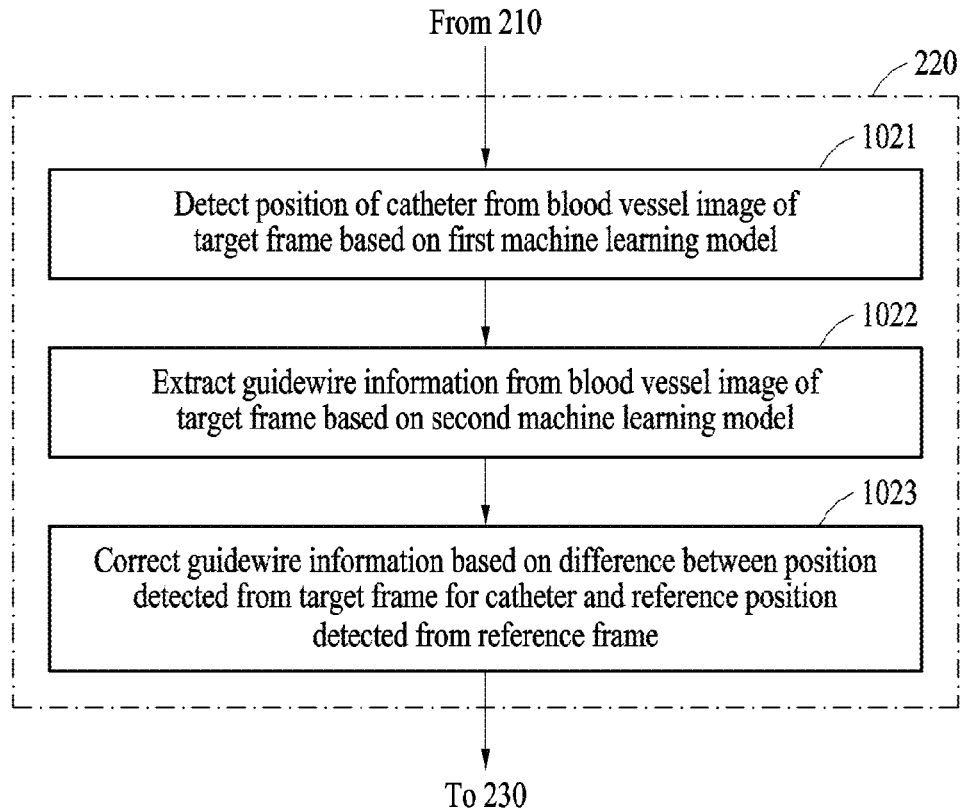
FIGS. 10 to 12 explain correction of guidewire information according to an example embodiment.
Figure 11:
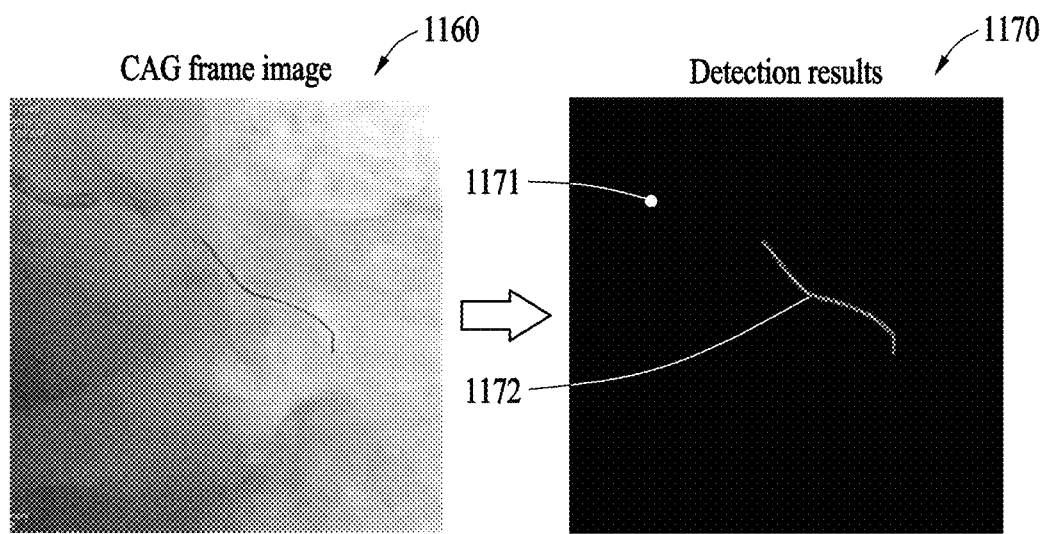
Figure 12:
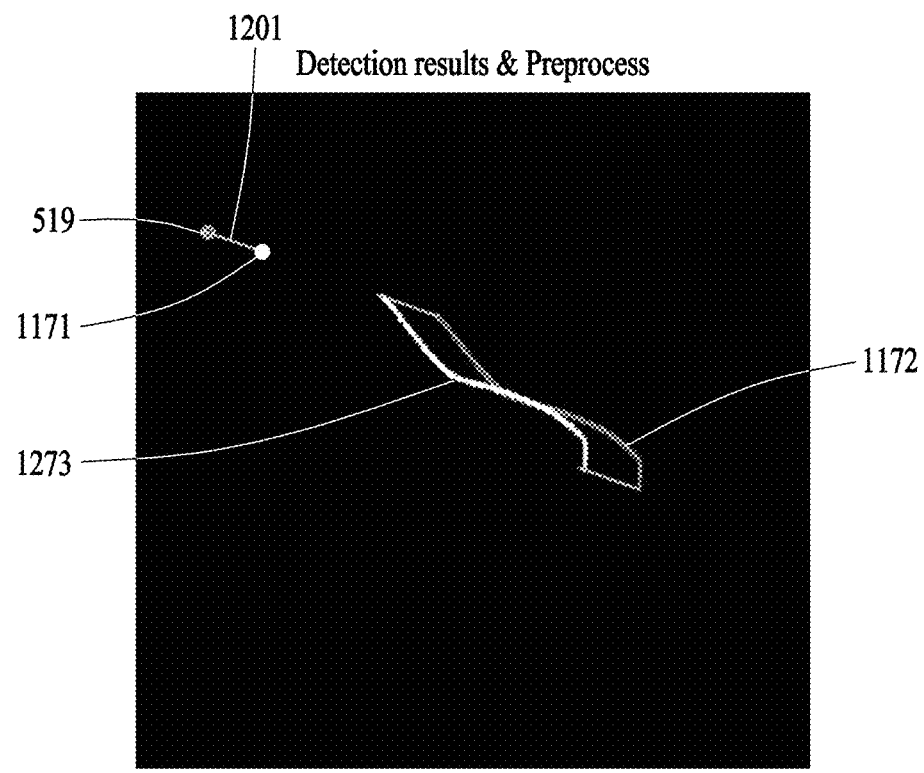
Figure 13:
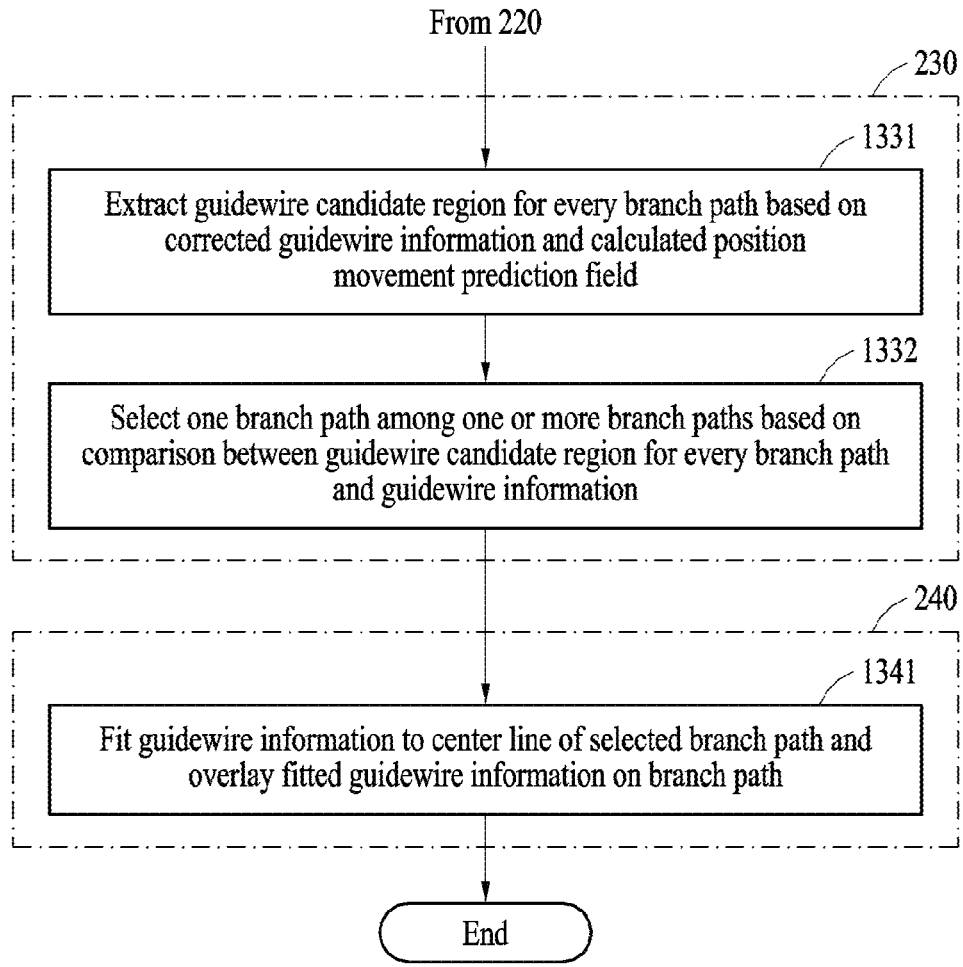
FIGS. 13 to 16 explain selection of branch path and visualization of guidewire information according to an example embodiment.

FIGS. 10 to 12 explain correction of guidewire information according to an example embodiment.

In step 1021, the electronic device may detect a catheter position 1171 of the target frame based on the first machine learning model from the blood vessel image 1160 of the target frame. As described above, the electronic device may detect the catheter position of the reference frame based on the first machine learning model, from the blood vessel image of the reference frame. In other words, the first machine learning model may be used to detect the catheter position from the reference frame and the target frame.

In step 1022, the electronic device may extract the guidewire information from the blood vessel image 1160 of the target frame based on a second machine learning model which is different from the first machine learning model. The second machine learning model is a model which is designed and trained to extract a guidewire from the blood vessel image and may include a neural network. The second machine learning model may output guidewire information of the target frame in response to an input of the blood vessel image 1160 of the target frame. The guidewire information is information about a part 1172 of the blood vessel image corresponding to the guidewire and may include information indicating at least one or a combination of two or more of a pixel, a point, and an area belonging to the guidewire in the image. The guidewire information may include a partial image in which the guidewire is segmented. For reference, the first machine learning model is a keypoint regional convolutional neural network (R-CNN) to output a point and the second machine learning model is a mask R-CNN to output a segmented area, but are not limited thereto.

Therefore, the electronic device may generate a detection result 1170 obtained by detecting a position 1171 of a tip of the catheter and a portion 1172 corresponding to the guidewire from the blood vessel image 1160 of the target frame (for example, a current frame) based on the first machine learning model and the second machine learning model.

Next, in step 1023, the electronic device may correct the guidewire information based on a difference between a position for the catheter detected from the target frame and a reference position detected from the reference frame. In other words, the electronic device may correct the guidewire information based on the difference 1201 between the catheter position 519 of the reference frame and the catheter position 1171 of the target frame. For example, as illustrated in FIG. 12, the electronic device may acquire the guidewire information 1273 corrected by moving a portion 1172 corresponding to the guidewire of the target frame by the difference 1201 (for example, a vector difference) between the catheter position 519 of the reference frame and the catheter position 1171 of the target frame.

FIGS. 13 to 16 explain selection of branch path and visualization of guidewire information according to an example embodiment.

In step 1331, the electronic device may extract a guidewire candidate region for one or more branch paths, based on the corrected guidewire information and the calculated position movement prediction field. The electronic device according to the example embodiment may extract a candidate region based on the position movement prediction field for one or more branch paths using the corrected guidewire information.

Figure 14:
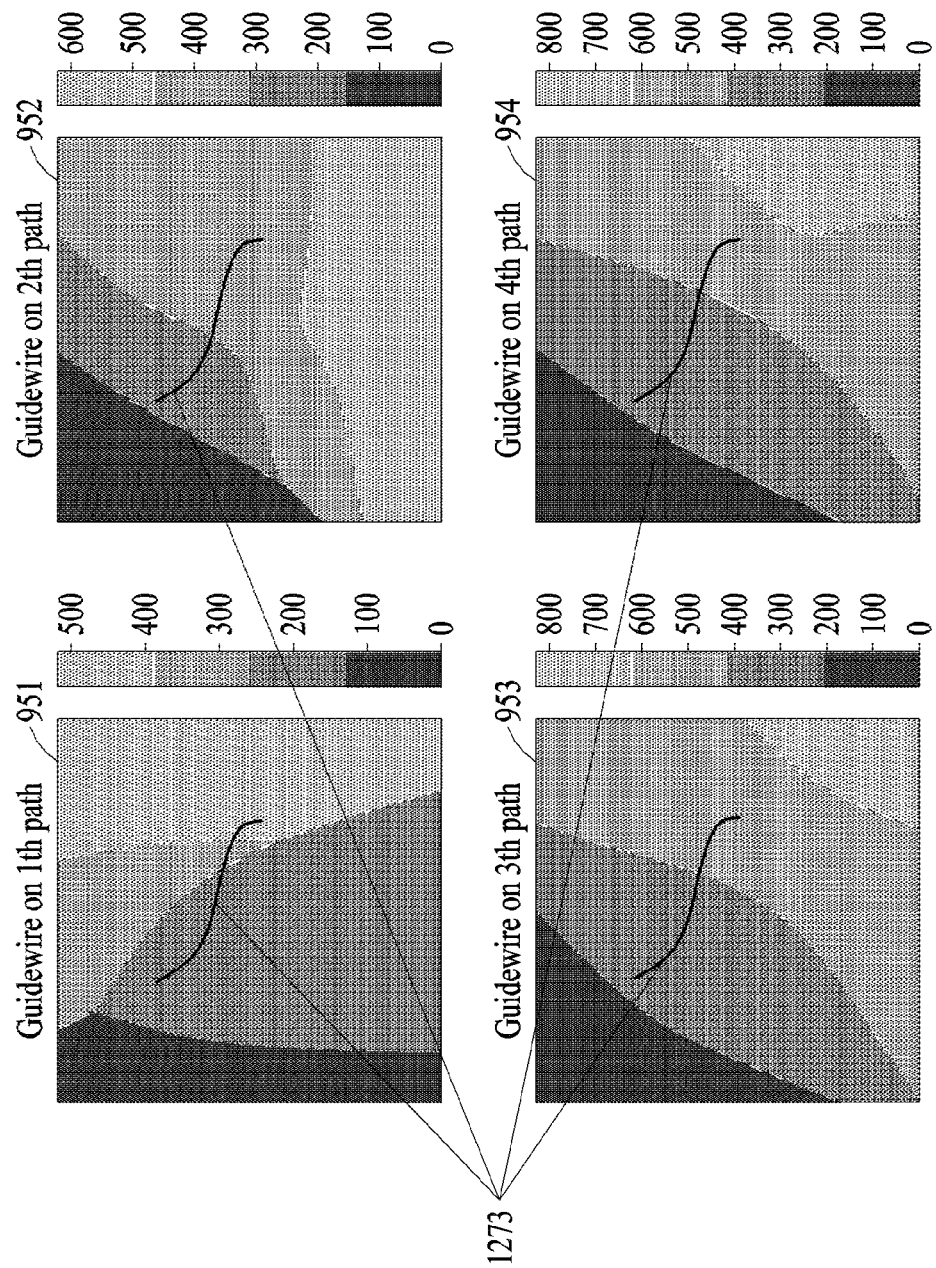

For example, the electronic device may map the corrected guidewire information on the position movement prediction field for each of one or more branch paths to acquire a plurality of predictive values corresponding to the guidewire in the corresponding branch path. As illustrated in FIG. 14, the electronic device may individually map the corrected guidewire information 1273 to the first position movement prediction field 951, the second position movement prediction field 952, the third position movement prediction field 953, and the fourth position movement prediction field 954. The electronic device may extract predictive values corresponding to a position to which the corrected guidewire information 1273 is mapped, from each position movement prediction field.

Figure 15:
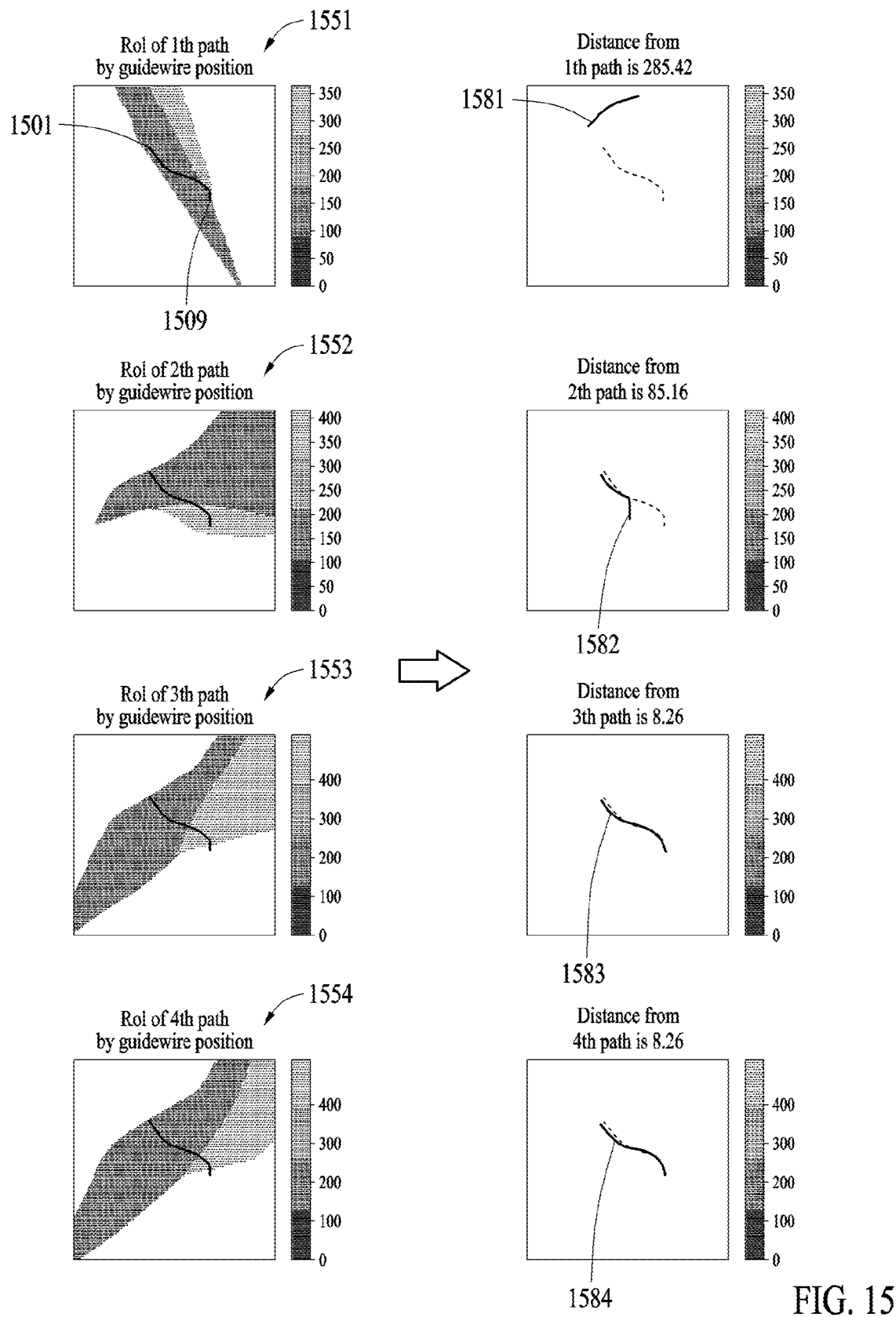
Figure 16:
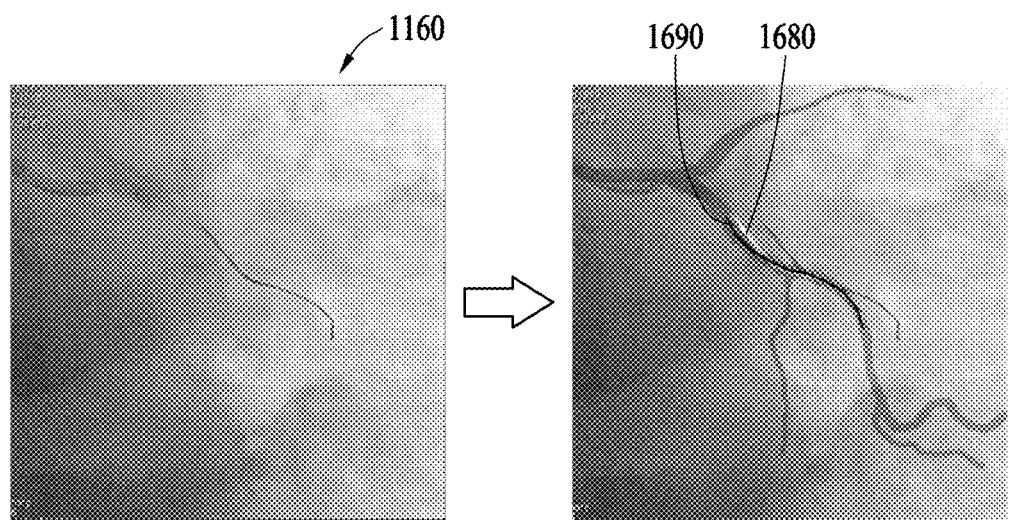

The electronic device may extract a guidewire candidate region of the corresponding branch path based on the plurality of predictive values acquired from the position movement prediction field of each branch path. The electronic device may extract the guidewire candidate region of the corresponding branch path based on a minimum value (for example, a minimum path length value) and a maximum value (for example, a maximum path length value) among the plurality of acquired predictive values. For example, the electronic device may determine the minimum value and the maximum value among position movement predictive values for every point belonging to the guidewire, for each branch path. As illustrated in FIG. 15, the electronic device may determine the minimum value 1501 and the maximum value 1509 among predictive values of points to which the corrected guidewire information is mapped in the first position movement prediction field 1551. The electronic device may determine the minimum value and the maximum value among predictive values to which the guidewire information in each branch path is mapped, also for the second position movement prediction field 1552, the third position movement prediction field 1553, and the fourth position movement prediction field 1554.

The electronic device may extract a candidate region from the minimum value to the maximum value which are determined as described above from the branch path length map of the corresponding branch path. The candidate region is a region indicating a portion in the corresponding branch path in which a guidewire of the current/target frame may potentially exist and may be also referred to as a candidate partial length map. The electronic device may extract a region between the minimum value and the maximum value determined for the first branch path 741 as described above with regard to FIG. 14, from the first branch path length map 831 acquired in FIG. 8, as a first candidate region 1581. Similarly, the electronic device may extract a region between the minimum value and the maximum value determined for the second branch path 742 according to the operation described above with regard to FIG. 14, from the second branch path length map 832, as a second candidate region 1582. The electronic device may extract a third candidate region 1583 between the minimum value and the maximum value in the corresponding branch path from the third branch path length map 833 and extract a fourth candidate region 1584 between the minimum value and the maximum value in the corresponding branch path from the fourth branch path length map 834.

In step 1332, the electronic device may select one branch path among one or more branch paths, based on comparison between the guidewire candidate region and the guidewire information for one or more branch paths. The electronic device according to the example embodiment may calculate a comparison score between the respective candidate region described in FIG. 15 and the corrected guidewire information. The electronic device may sort the comparison scores calculated for the respective candidate regions and determine one candidate region among the plurality of candidate regions based on the sorted order of the comparison scores. The electronic device may select a branch path corresponding to the determined candidate region. The electronic device may calculate a distance score or a similarity score as the comparison score. The distance score is a score indicating a difference level between the candidate region and the guidewire information and the larger the similarity, the lower the distance score. The similarity score is a score indicating a similarity level between the candidate region and the guidewire information and the larger the similarity, the higher the similarity score. In the present specification, the distance score will be mainly described, but the comparison score is not limited thereto.

For example, the electronic device may sample the candidate region acquired for one or more branch paths at every first interval to acquire candidate sampling points of each candidate region. The electronic device may sample the corrected guidewire information at every second interval to acquire guidewire sampling points of the guidewire information. The first interval may be an interval obtained by equally dividing a length according to the branch path (for example, the blood vessel center line) from a point corresponding to the minimum value of the candidate region to the maximum value by n. Here, n may be an integer of 2 or larger. The second interval may be an interval obtained by equally dividing a length according to the branch path (for example, the blood vessel center line or a guidewire center line) of the guidewire region corresponding to the corrected guidewire information by n. Accordingly, the electronic device may extract n sampling points for each of the candidate regions and the guidewire information.

According to the example embodiment, the electronic device may calculate a distance score between the guidewire candidate region and the guidewire information for one or more branch paths. For example, the electronic device may calculate a sum of distances between n candidate sampling points of each candidate region and n guidewire sampling points in the corrected guidewire information as the above-described distance score. The electronic device may calculate the distance between the sampling points and the sum of the distances using various curve distance techniques such as Euclidean distance, Hausdorff distance, and Frechet distance. The electronic device may select a branch path having a candidate region indicating the highest distance score among the guidewire candidate regions.

Further, the electronic device may calculate the comparison score (for example, the distance score) based on not only a trial in the target frame, but also a trial in a past frame. The electronic device according to the example embodiment may select a branch path based on a comparison history between the guidewire candidate region of each branch path in a previous frame of the target frame and the guidewire information and a comparison result between the guidewire candidate region of each branch path in the target frame and the guidewire information.

For example, the electronic device may calculate a fused result value of a comparison score (for example, a distance score) for each trial based on the trial history. The fused result value may be calculated based on various weighting functions. For example, the fused result value may be a weighted sum. The electronic device may select one candidate branch among a plurality of candidate branches based on the calculated result value.

The electronic device may apply a first weight to a first comparison score in a first previous frame which precedes the target frame by a first frame difference. The electronic device may apply a second weight which is different from the first weight to a second comparison score in a second previous frame which precedes the target frame by a second frame difference which is larger than the first frame difference. For example, when the comparison score is a distance score, the electronic device may apply the second weight which is larger than the first weight to the second comparison score. For example, the electronic device may apply a higher weight to the comparison score of the previous frame than the comparison score of the target frame. The larger the frame difference between the current frame and the previous frame, the higher the weight to be applied by the electronic device. The more temporally adjacent to the current frame, that is, the smaller the frame difference between the current frame and the previous frame, the lower the weight to be applied. The electronic device may select the branch path using a fused result value based on a first partial score obtained by applying a first weight to the first comparison score and a second partial score obtained by applying a second weight to the second comparison score. Hereinafter, a distance score will be described as an example of the comparison score.

For example, the electronic device may acquire a distance score as represented in Table 1, from a T-4-th frame to a T-th frame (for example, the target frame) for four branch paths.

TABLE 1

| Timestep | T - 4 | T - 3 | T - 2 | T - 1 | T |
|---|---|---|---|---|---|
| Path 1. | 206.35 | 210.15 | 177.55 | 239.74 | 285.42 |
| Path 2. | 49.41 | 40.89 | 39.01 | 59.44 | 85.16 |
| Path 3. | 7.29 | 12.01 | 35.67 | 13.68 | 8.26 |
| Path 4. | 7.29 | 12.01 | 35.67 | 13.68 | 8.26 |

The electronic device may calculate a linear weighted average for each branch path. For example, a weight for the distance score of the T-4-th frame is 5, a weight for the distance score of the T-3-th frame is 4, a weight for the T-2-th frame is 3, a weight for the T-1-th frame is 2, and a weight for the T-th frame is 1. The electronic device may calculate a weighted distance score for the first branch path based on the trial history as Distance from Path 1=5×206.35+4×210.15+3×177.55+2×239.74+1×285.42=3169.9. Similarly, the electronic device may calculate Distance from Path 2=5×49.41+4×40.89+3×39.01+2×59.44+1×85.16=731.68 as a weighted distance score for the second branch path, Distance from Path 3=5×7.29+4×12.01+3×35.67+2×13.68+1×8.26=227.12 as a weighted distance score for the third branch path, and Distance from Path 4=5×7.29+4×12.01+3×35.67+2×13.68+1×8.26=227.12 as a weighted distance score for the fourth branch path. Accordingly, the electronic device may determine that the guidewire is located in the third branch path and/or the fourth branch path. A location where the guidewire is disposed may be a region shared by the third branch path and the fourth branch path before being branched. As described above, even though an error temporally occurs in the target frame (for example, the current frame), the electronic device may exactly determine a branch where the guidewire is located by considering the trial history.

For reference, a linear weighted sum has been described as a weighted distance score, but is not limited thereto. An even weight (for example, the same weight (1×100+1×105+1×200+1×30=435 is applied for all time frames), a ramp weight (for example, a weight which is ramped up, such as multiples of 2 is applied by 8×100+4×105+2×200+1×30=1650), and a non-linear weight (for example, a weight according to the non-linear function f(x) is applied by f(1)×100+f(2)×105+f(3)×200+f(4)×30) may be used.

Next, in step 1341, the electronic device may fit the guidewire information to the center line of the selected branch path and overlay the fitted guidewire information on the branch path. The electronic device may fit the guidewire information to the center line of the selected branch path. For example, the electronic device may calculate a coordinate transformation matrix between the guidewire sampling points of the guidewire information and the sampling points of the center line in the candidate region. The coordinate transformation matrix may indicate a matrix for rotation and/or translation to fit the guidewire to the center line of the blood vessel. The electronic device may apply the calculated coordinate transformation matrix to pixels included in the corrected guidewire information.

The display of the electronic device may overlay the fitted guidewire information 1690 on the branch path. In other words, the electronic device may provide the guidewire acquired from the blood vessel image 1160 of the target frame which is a frame after the reference frame so as to be fitted to the center line 1680 of the corresponding blood vessel. For example, the electronic device may overlay the above-described coordinate-transformed guidewire on the blood vessel image by a graphic expression that changes at least one of a color, a frame, a thickness, and a brightness, so as to be distinguished from the guidewire before correction, acquired from the target frame.

The operations described above in FIGS. 10 to 16 may be performed for every frame. For example, the operations described in FIGS. 10 to 16 may be performed in a series of target frames, after the reference frame at which the contrast is injected. When the contrast is injected again, the timing when the contrast is injected may be set as a new reference frame. When the contrast is newly injected, the operations described in FIGS. 1 to 9 may be performed and the operations described in FIGS. 10 to 16 may be performed for every target frame until the contrast is injected again. In other words, the position movement prediction field which is acquired in the corresponding reference frame may be reused until the reference frame is reset.

Figure 17:
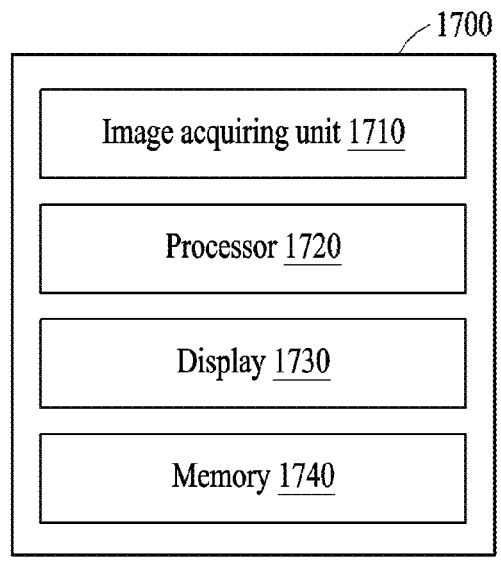
FIG. 17 is a block diagram explaining a guidewire detecting device according to an example embodiment.

FIG. 17 is a block diagram explaining a guidewire detecting device according to an example embodiment.

The electronic device 1700 may include an image acquiring unit 1710, a processor 1720, a display 1730, and a memory 1740. The electronic device 1700 may also be referred to as a guidewire detecting device.

The image acquiring unit 1710 may acquire a blood vessel image of a reference frame and a blood vessel image of a target frame. The image acquiring unit 1710 according to the example embodiment may acquire coronary angiography (CAG) images of the reference frame and the target frame as blood vessel images of the reference frame and the target frame. The image acquiring unit 1710 may capture a blood vessel image or receive a blood vessel image from an external imaging device.

The processor 1720 may acquire a blood vessel image of the reference frame. The processor 1720 may extract a blood vessel region image in which the blood vessel region is segmented, from a blood vessel image of the reference frame. The processor 1720 may detect a position of the catheter based on the first machine learning model from the blood vessel image of the reference frame to set the position as a reference position. The processor 1720 may generate the entire path length map indicating a path length from a start position set using the reference position to points in the blood vessel region. The processor 1720 may acquire a branch path length map for each of one or more branch paths from the generated entire path length map. The processor 1720 may calculate a position movement prediction field (length weight field) of the corresponding branch path based on the branch path length map for each of one or more branch paths. The processor 1720 may detect the position of the catheter based on the first machine learning model from the blood vessel image of the target frame. The processor 1720 may extract the guidewire information based on the second machine learning model from the blood vessel image of the target frame. The processor 1720 may correct the guidewire information based on a difference between a position for the catheter detected from the target frame and a reference position detected from the reference frame. The processor 1720 may extract a guidewire candidate region for one or more branch paths, based on the corrected guidewire information and the calculated position movement prediction field. The processor 1720 may select one branch path among one or more branch paths, based on comparison between the guidewire candidate region and the guidewire information for one or more branch paths. However, the operation of the processor 1720 is not limited to the operation described above, but the processor may perform the operations described above in FIGS. 1 to 16.

The display 1730 may visualize the guidewire information in the selected branch path.

The memory 1740 may store the first machine learning model and the second machine learning model. Further, the memory 1740 may temporarily and/or permanently store data and/or information required to perform the guidewire detecting method.

The example embodiments described above may be implemented by a hardware component, a software component, and/or a combination of the hardware component and the software component. For example, the device, the method, and the components described in the example embodiments may be implemented, for example, using a general purpose computer or a special purpose computer such as a processor, a controller, an arithmetic logic unit (ALU), a digital signal processor, a microcomputer, a field programmable gate array (FPGA), a programmable logic unit (PLU), a microprocessor, or any other device which executes or responds instructions. The processing device may perform an operating system (OS) and a software application which is executed on the operating system. Further, the processing device may access, store, manipulate, process, and generate data in response to the execution of the software. For ease of understanding, it may be described that a single processing device is used, but those skilled in the art may understand that the processing device may include a plurality of processing elements and/or a plurality of types of processing element. For example, the processing device may include a plurality of processors or include one processor and one controller. Further, another processing configuration such as a parallel processor may be allowed.

The software may include a computer program, a code, an instruction, or a combination of one or more of them and configure the processing device to be operated as desired or independently or collectively command the processing device. The software and/or data may be permanently or temporarily embodied in an arbitrary type of machine, component, physical device, virtual equipment, computer storage medium, or device, or signal wave to be transmitted to be interpreted by a processing device or provide instruction or data to the processing device. The software may be distributed on a computer system connected through a network to be stored or executed in a distributed manner. The software and data may be stored in a computer readable recording medium.

The method according to the example embodiment may be implemented as a program instruction which may be executed by various computers to be recorded in a computer readable medium. The computer readable medium may include the program instruction, a data file, or a data structure alone or in combination and the program instruction stored in the medium may be specifically designed and configured for the example embodiment or known to be available to those skilled in the art of computer software. Examples of the computer readable recording medium include magnetic media such as a hard disk, a floppy disk, or a magnetic tape, optical media such as a CD-ROM or a DVD, magneto-optical media such as a floptical disk, and a hardware device which is specifically configured to store and execute the program instruction such as a ROM, a RAM, and a flash memory. Examples of the program instruction include not only a machine language code which is created by a compiler but also a high level language code which may be executed by a computer using an interpreter.

The hardware device may operate as one or a plurality of software modules in order to perform the operation of the example embodiment and vice versa.

As described above, although example embodiments have been described by limited drawings, those skilled in the art may apply various technical modifications and changes based on the above description. For example, even when the above-described techniques are performed by different order from the described method and/or components such as systems, structures, devices, or circuits described above are coupled or combined in a different manner from the described method or replaced or substituted with other components or equivalents, the appropriate results can be achieved.

Therefore, other implements, other example embodiments, and equivalents to the claims are within the scope of the following claims.

What is claimed is:

1. An electronic device, comprising:
a processor configured to generate a position movement prediction field indicating prediction of a potential positional change of a branch path by a patient's biological activity for one or more branch paths based on a blood vessel image of a reference frame, to correct guidewire information extracted from a blood vessel image of a target frame with respect to a catheter position of the reference frame, and to select a branch path to dispose the guidewire information, among one or more branch paths of a blood vessel region based on the position movement prediction field and the corrected guidewire information; and
a display configured to visualize the guidewire information on the selected branch path,
wherein the processor generates an entire path length map indicating a path length to points in a segmented blood vessel region from the blood vessel image of the reference frame and generates the position movement prediction field for each of one or more branch paths of the blood vessel region based on the entire path length map.

2. The electronic device of claim 1, further comprising:
an image acquiring unit configured to acquire coronary angiographic images of the reference frame and the target frame as blood vessel images of the reference frame and the target frame.

3. The electronic device of claim 1, wherein the processor extracts a blood vessel region image in which the blood vessel region is segmented from the blood vessel image of the reference frame, detects a catheter position from the blood vessel image of the reference frame based on a first machine learning model to set the catheter position as a reference position, and generates an entire path length map indicating a path length from a start position set using the reference position to points in the blood vessel region.

4. The electronic device of claim 1, wherein the processor acquires a branch path length map for each of one or more branch paths from the generated entire path length map and generates a position movement prediction field of the corresponding branch path based on the branch path length map for each of the one or more branch paths.

5. The electronic device of claim 1, wherein the processor determines a same value as a path length value of a corresponding point in the position movement prediction field for each branch path, as a predictive value of a position predicted that each point in a corresponding branch path is potentially moved by a biological activity.

6. The electronic device of claim 5, wherein the processor determines each predictive value of the position movement prediction field based on Euclidean distance transform between each point in the branch path and a point outside the branch path.

7. The electronic device of claim 1, wherein the processor detects a catheter position of the reference frame from the blood vessel image of the reference frame based on a first machine learning model, detects a catheter position of the target frame from the blood vessel image of the target frame based on the first machine learning model, and corrects the guidewire information based on a difference between the catheter position of the reference frame and the catheter position of the target frame.

8. The electronic device of claim 7, wherein the processor extracts the guidewire information from the blood vessel image of the target frame based on a second machine learning model which is different from the first machine learning model.

9. The electronic device of claim 1, wherein the processor extracts a guidewire candidate region for the one or more branch paths based on the corrected guidewire information and the generated position movement prediction field and selects one branch path among the one or more branch paths, based on comparison between the guidewire candidate region for the one or more branch paths and the guidewire information.

10. The electronic device of claim 9, wherein the processor acquires a plurality of predictive values corresponding to a guidewire in the corresponding branch path by mapping the corrected guidewire information on the position movement prediction field for each of the one or more branch paths and extracts the guidewire candidate region of the corresponding branch path based on the plurality of acquired predictive values.

11. The electronic device of claim 10, wherein the processor extracts a guidewire candidate region of the corresponding branch path based on a minimum value and a maximum value among the plurality of acquired predictive values.

12. The electronic device of claim 9, wherein the processor calculates a distance score between the guidewire candidate region for the one or more branch paths and the guidewire information and selects a branch path having a candidate region indicating a highest distance score, among the guidewire candidate regions.

13. The electronic device of claim 9, wherein the processor selects a branch path based on a comparison history between the guidewire candidate region of each branch path in a previous frame of the target frame and the guidewire information and a comparison result between the guidewire candidate region of each branch path in the target frame and the guidewire information.

14. The electronic device of claim 13, wherein the processor applies a first weight to a first comparison score in a first previous frame which precedes the target frame by one frame difference, applies a second weight which is different from the first weight to a second comparison score in a second previous frame which precedes the target frame by a second frame difference which is larger than the first frame difference, and selects the branch path using a fused result value based on a first partial score obtained by applying the first weight to the first comparison score and a second partial score obtained by applying the second weight to the second comparison score.

15. The electronic device of claim 1, wherein the processor fits the guidewire information to a center line of the selected branch path and the display overlays the fitted guidewire information onto the branch path.

16. The electronic device of claim 1, wherein the target frame is a frame after the reference frame.

17. The electronic device of claim 1, wherein the reference frame is a frame corresponding to a timing when a contrast is injected into a patient.

18. A guidewire detecting method performed by an electronic device, the method comprising:
generating a position movement prediction field indicating prediction of a potential positional change of a branch path by a patient's biological activity for one or more branch paths based on a blood vessel image of a reference frame;
correcting guidewire information extracted from a blood vessel image of a target frame with respect to a catheter position of the reference frame;
selecting a branch path to dispose the guidewire information, among one or more branch paths of a blood vessel region based on the position movement prediction field and the corrected guidewire information; and
visualizing the guidewire information on the selected branch path,
wherein the generating of the position movement prediction field includes:
generating an entire path length map indicating a path length to points in a segmented blood vessel region from the blood vessel image of the reference frame; and
generating the position movement prediction field for each of one or more branch paths of the blood vessel region based on the entire path length map.

19. A non-transitory computer readable medium to be coupled to hardware to execute the method of claim 18.

* * * * *